United States Patent [19]

Bellhouse

[11] 4,182,653

[45] Jan. 8, 1980

[54] MASS TRANSFER BETWEEN FLUIDS AND APPARATUS THEREFOR

[75] Inventor: Brian J. Bellhouse, Wendlebury, England

[73] Assignee: National Research Development Corporation, London, England

[21] Appl. No.: 843,932

[22] Filed: Oct. 20, 1977

[30] Foreign Application Priority Data

Oct. 22, 1976 [GB] United Kingdom ............... 43977/76

[51] Int. Cl.$^2$ .............................................. C12K 9/00
[52] U.S. Cl. .......................................... 435/2; 422/48
[58] Field of Search ................................ 195/1.7, 1.8; 23/258.5 M, 258.5 MH; 422/48

[56] References Cited

U.S. PATENT DOCUMENTS

| 3,332,746 | 7/1967 | Claff et al. ........................... 23/258.5 |
| 3,484,211 | 12/1969 | Mon et al. ............................ 23/258.5 |

*Primary Examiner*—Sam Rosen
*Attorney, Agent, or Firm*—Cushman, Darby & Cushman

[57] ABSTRACT

The oxygenation and removal of carbon dioxide from blood by simultaneous mass transfer through a microporous membrane is improved by pulsing the flow of oxygenating gas over the membrane. This avoids the progressive reduction in carbon dioxide transfer rate which otherwise occurs with steady gas flow and allows such transfer rate to be maintained at an acceptable level.

9 Claims, 6 Drawing Figures

| TIME MIN. | BLOOD FLOW ml./min. | VENOUS BLOOD | | | | | | ARTERIAL BLOOD | | | | | 100% O₂ FLOW ml./min. | GAS TRANSFER | | | $r_{CO_2}/r_{O_2}$ |
|---|---|---|---|---|---|---|---|---|---|---|---|---|---|---|---|---|---|
| | | $pO_2$ | $pCO_2$ | pH | Hgn | %O₂ | °C | $pO_2$ | $pCO_2$ | pH | %O₂ | °C | | % CO₂ TRANSFER | CO₂ TRANSFER ml./min. | O₂ TRANSFER ml./min. | |
| 0 | 500 | 41.8 | 38.9 | 7.350 | 13.6 | 66 | 36 | 80.7 | 36.0 | 7.355 | 93 | 35.5 | 14600 | .08 | 11.68 | 25.87 | 0.45 |
| 15 | 500 | 34.8 | 42.6 | 7.327 | 13.6 | 52 | 36 | 52.7 | 40.5 | 7.322 | 77 | 36 | 15200 | .08 | 13.68 | 24.15 | 0.57 |
| 31 | 500 | 33.4 | 41.3 | 7.329 | 13.5 | 50 | 36.5 | 50.9 | 39.2 | 7.327 | 76 | 36.5 | 14300 | .09 | 12.87 | 24.85 | 0.52 |
| 53 | 500 | 45.2 | 45.6 | 7.406 | 13.6 | 74 | 36.5 | 85.5 | 41.8 | 7.446 | 95 | 36.5 | 14400 | .09 | 12.96 | 20.70 | 0.63 |
| 70 | 500 | 34.9 | 38.2 | 7.463 | 13.6 | 62 | 36.7 | 55.4 | 34.4 | 7.470 | 87 | 36.7 | 15000 | .08 | 12.00 | 23.55 | 0.51 |
| 88 | 500 | 29.8 | 42.9 | 7.411 | 13.6 | 48 | 35.8 | 52.5 | 40.6 | 7.425 | 83 | 36.0 | 9600 | .12 | 12.48 | 33.30 | 0.37 |
| 105 | 500 | 34.1 | 49.1 | 7.381 | 13.6 | 54 | 35.2 | 57.2 | 46.1 | 7.381 | 84 | 35.5 | 9600 | .12 | 12.48 | 28.65 | 0.44 |
| 121 | 500 | 41.0 | 41.3 | 7.429 | 13.7 | 70 | 36.0 | 85.7 | 38.6 | 7.432 | 95 | 36.5 | 9400 | .11 | 10.34 | 24.90 | 0.42 |
| 139 | 500 | 34.9 | 34.5 | 7.476 | 13.9 | 64 | 36.0 | 65.8 | 32.9 | 7.488 | 92 | 36.2 | 9600 | .09 | 9.60 | 28.10 | 0.34 |
| 154 | 750 | 34.4 | 40.7 | 7.439 | 13.9 | 60 | 36.7 | 49.2 | 39.9 | 7.428 | 80 | 37.0 | 9600 | .13 | 10.56 | 29.85 | 0.35 |
| 166 | 750 | 36.4 | 41.0 | 7.423 | 13.9 | 62 | 36.5 | 51.1 | 39.5 | 7.427 | 82 | 37.2 | 4700 | .28 | 12.69 | 28.80 | 0.44 |
| 185 | 1000 | 37.1 | 42.4 | 7.409 | 13.8 | 62 | 36.7 | 48.9 | 41.6 | 7.411 | 77 | 37.4 | 4700 | .25 | 11.28 | 31.90 | 0.35 |
| | | | | | | | | | | | | | | Averages | 11.89 | 27.05 | 0.45 |

| TIME MIN. | BLOOD FLOW ml./min. | VENOUS BLOOD | | | | | | ARTERIAL BLOOD | | | | | GAS TRANSFER | | | | $r_{CO_2}/r_{O_2}$ |
|---|---|---|---|---|---|---|---|---|---|---|---|---|---|---|---|---|---|
| | | $pO_2$ | $pCO_2$ | pH | Hgn | $\%O_2$ | °C | $pO_2$ | $pCO_2$ | pH | $\%O_2$ | °C | 100% $O_2$ FLOW ml./min. | % $CO_2$ TRANSFER | $CO_2$ TRANSFER ml./min. | $O_2$ TRANSFER ml./min. | |
| 0 | 700 | 67.5 | 47.9 | 7.229 | 13.0 | 88 | 35 | 209.5 | 38.6 | 7.260 | 99 | 34.5 | 4600 | .68 | 31.26 | 14.48 a) | — |
| 22 | 700 | 40.7 | 44.8 | 7.352 | 12.9 | 64 | 37 | 62.8 | 39.5 | 7.369 | 87 | 37 | 4500 | .59 | 26.33 | 29.41 | 0.9 |
| 78 | 700 | 45.8 | 51.3 | 7.261 | 12.7 | 71 | 35.2 | 73.9 | 44.9 | 7.284 | 92 | 35.3 | 4300 | .64 | 27.57 | 25.95 | 1.06 |
| 99 | 700 | 40.6 | 50.6 | 7.263 | 12.7 | 59 | 36.3 | 60.4 | 43.0 | 7.305 | 84 | 36.4 | 4300 | .68 | 29.26 | 30.80 | 0.95 |
| 120 | 700 | 39.2 | 49.1 | 7.372 | 12.4 | 64 | 36.7 | 62.7 | 42.4 | 7.413 | 89 | 36.8 | 4100 | .69 | 28.34 | 30.65 | 0.92 |
| 149 | 700 | 38.8 | 48.8 | 7.354 | 12.4 | 62 | 36.6 | 61.6 | 42.4 | 7.391 | 88 | 36.8 | 4700 | .65 | 30.65 | 30.95 | 0.99 |
| 212 | 600 | 44.0 | 48.8 | 7.347 | 12.5 | 71 | 36.1 | 97.2 | 39.8 | 7.427 | 97 | 36.0 | 6200 | .47 | 29.41 | 27.03 | 1.09 |
| 232 | 600 | 44.3 | 48.0 | 7.388 | 12.6 | 69 | 36.5 | 79.2 | 39.8 | 7.405 | 94 | 36.3 | 6000 | .49 | 29.65 | 27.03 | 1.1 |
| 258 | 600 | 39.1 | 46.2 | 7.345 | 12.3 | 62 | 36.6 | 76.5 | 37.8 | 7.409 | 94 | 36.5 | 6400 | .47 | 30.34 | 32.65 | 0.93 |
| | | | | | | | | | | | | | Averages | | 29.02 | 29.31 | 0.99 |

MASS TRANSFER BETWEEN FLUIDS AND APPARATUS THEREFOR

The present invention relates generally to membrane oxygenators (artificial lungs) and, more particularly, to apparatus for, and methods of, improving the rate of transfer of certain gases to and from the blood.

Oxygenators are used to add oxygen to, and remove carbon dioxide from, a patient's blood in those instances where his lungs cannot perform their usual gas exchange function. In open heart surgery, for example, where the heart is temporarily unable to pump blood through the patient's lungs to be oxygenated, the patient's blood is pumped through an extracorporeal circuit which includes an oxygenator.

Several types of oxygenators are presently available, and among these is the membrane oxygenator. A membrane oxygenator, in its basic form, comprises first and second conduits separated by a transfer membrane which is permeable to oxygen and carbon dioxide. During use of the membrane oxygenator, an oxygenating gas is caused to pass through one of the conduits (sometimes referred to as the oxygenating gas passageway) while the patient's blood is caused to flow simultaneously through the other conduit (sometimes referred to as the blood passageway). Oxygen passes from the oxygenating gas through the transfer membrane and into the blood; simultaneously, carbon dioxide passes from the blood through the transfer membrane and into the stream of oxygenating gas. Thus, blood leaving the oxygenator has a higher oxygen content, and a lower carbon dioxide content, than blood entering the oxygenator. Conversely, the oxygenating gas leaving the oxygenator is poorer in oxygen and richer in carbon dioxide as compared to when it entered the oxygenator.

Recently microporous membranes, i.e. membranes having a large number of small holes, have become available for use in blood oxygenators. Such membranes are preferred for use in membrane oxygenators because the rates of transfer of oxygen and carbon dioxide therethrough are significantly higher than the corresponding rates of transfer through the "solid" membranes (such as those comprising silicone rubber, silicone rubber/polycarbonate polymers, or poly[alkylsulfones]) previously used in oxygenators. The use of microporous membranes in blood oxygenators, however, gives rise to a problem which had not existed when solid membranes were used. It has been observed that in a blood oxygenator which employs a microporous membrane, the rate of transfer of carbon dioxide from venous blood is progressively decreased the longer the oxgenator is in operation. This decrease in the rate of transfer of carbon dioxide has been observed even after relatively brief periods of operation of the oxygenator.

Failure to remove sufficient amounts of carbon dioxide from the venous blood may lead to serious consequences for the patient. The blood performs its functions most effectively at a pH of about 7.4. If carbon dioxide is not removed from the blood at an acceptable rate, its concentration in the blood necessarily increases and it reacts with water in the blood to lower the blood pH. As carbon dioxide levels in the blood increase, the pH of the blood is progressively decreased, and the oxygen carrying ability of the blood is quite noticeably and very undesirable reduced.

In addition to the aforementioned decrease in the rate of transfer of carbon dioxide which is encountered in a blood oxygenator comprising a microporous membrane, it has also been observed that concurrently therewith there is a gradual build-up of water in the form of droplets in the gas passageway of the oxygenator. This is because microporous membranes, in addition to permitting high rates of transfer of oxygen and carbon dioxide, also permit the transfer of water vapour therethrough. Thus, when microporous membranes are used in blood oxygenators, a certain amount of water is transferred from the blood through the membrane and into the gas passageway where it condenses in the form of water droplets. Owing to its very high solubility in water, the carbon dioxide passing through the membrane into the gas passageway readily dissolves in the condensed water droplets. It is believed that this increases the partial pressure of carbon dioxide in the gas passageway, which in turn reduces the carbon dioxide partial pressure gradient driving carbon dioxide out of the blood, thus accounting for the observed decrease in the rate of transfer of carbon dioxide through the membrane.

In the lungs of a human patient, the ratio of the rate of transfer of carbon dioxide to the rate of transfer of oxygen (hereinafter "$r_{CO_2}/r_{O_2}$") averages about 0.8:1. It is commonly accepted that in a blood oxygenator the ratio of the rate of transfer of carbon dioxide to the rate of transfer of oxygen should be in the range of about 0.75:1 to about 1:1.

Many of the surgical procedures involving the use of a blood oxygenator are carried out at normal body temperature, i.e., at about 37° C. At such temperatures, and after a very brief period in which carbon dioxide is transferred at a physiologically acceptable rate, the rate of transfer of carbon dioxide in a microporous membrane oxygenator is found to decrease markedly and the aforementioned ratio $r_{CO_2}/r_{O_2}$ decreases to a value of 0.5 or even lower. Such values are, of course, unacceptably low from the viewpoint of maintaining the desired physiologic conditions. This decrease in the rate of transfer of carbon dioxide is temperature dependent and the problem has been observed at temperatures as low as 26°–28° C.

It is believed that the carbon dioxide transfer rate problem could perhaps be alleviated by increasing the rate of flow of the oxygenating gas. However, this approach is thought to be impractical in that the flow rate of the oxygenating gas should not be increased to a point where the pressure associated with said oxygenating gas exceeds the pressure of the blood in the blood passageway. This is because there might then be a distortion of the membrane which in turn would lead to an undesirable distortion of the blood passageway. Worse still, the increase in pressure associated with increasing the rate of flow of the oxygenating gas could lead to the formation of bubbles of oxygen gas in the blood being oxygenated. In addition, high flow rates would be unnecessarily wasteful of oxygenating gas.

It is thought that the carbon dioxide transfer rate problem could be solved by carefully matching the temperature of the blood, oxygenating gas, and the membranes and its supports. Such a solution, however, would involve complex equipment and operating conditions and would be far from generally satisfactory. Such an approach would take on an added degree of difficulty in those cases in which the surgeon deemed it necessary or desirable to lower and raise the temperature of the patient's blood during the course of surgery.

In accordance with the present invention there is provided a method and apparatus which greatly reduces the occurrence of the above noted problem of decrease in the rate of transfer of carbon dioxide. The invention rests on the finding that the rate of transfer of carbon dioxide through a microporous membrane in a blood oxygenator can be maintained at acceptable levels by pulsing the flow of the oxygenating gas, even when the integrated flow rates of the oxygenating gas are low. In experiments where the oxygenating gas was not pulsed at the outset of an oxygenation run and a decrease in the rate of carbon dioxide transfer was encountered, the rate of transfer of carbon dioxide was thereafter restored to acceptable levels by causing the oxygenating gas to flow through the gas passageways of the oxygenator in pulsatile flow. While the reason for these advantageous results is not fully understood, it is believed to arise from the generation, by the pulsing, of high instantaneous pressure gradients in the gas flow. Another possible causory factor is the generation of high frequency components of force which vibrate the droplets in the gas passageway of the oxygenator. It has been observed that the beneficial effects of pulsing the oxygenating gas are more pronounced as the pulsatile or interrupting action approaches that of a square wave.

In initial development of the invention the required pulsatile action has been effected by regularly interrupting the oxygenating gas flow. The use of a solenoid valve connected serially in the gas supply line and actuated by an electric timing device has proved suitable for this purpose and provides a substantially square waveform in operation. However, it may be preferred to employ a piston pump connected in parallel with a primary gas supply line otherwise operable to provide a steady gas flow, so that the latter flow continues in the event of a malfunction of the gas pulse generator.

In development of the invention to date it has been found that a pulsatile action producing a pressure change within the oxygenator of 20 to 30 mm Hg, and usually about the latter value, has resulted in droplet clearance without exceeding the associated pressure in the blood passageway.

The invention will be better understood upon reading the following detailed description and upon reference to the appended drawings, in which:

FIG. 1 schematically illustrates one embodiment of apparatus according to the present invention;

FIG. 4 is a table of data and results obtained by operation of the embodiment of FIG. 1 in one mode;

FIG. 5 is a similar table relating to another operational mode; and

FIG. 6 schematically illustrates another embodiment.

Figure 1:
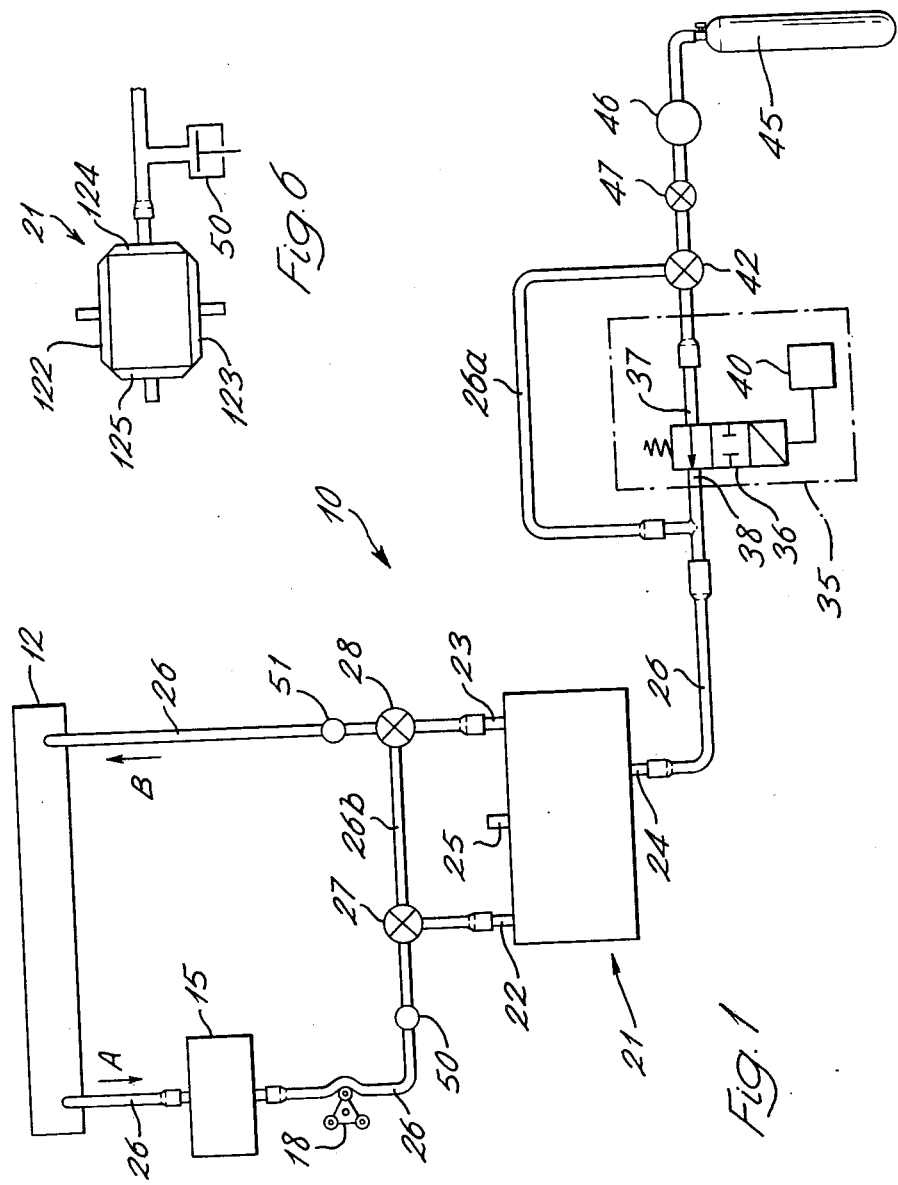

FIG. 1 illustrates an extra-corporeal apparatus and circuit for oxygenating the venous blood of an animal and returning oxygenated blood to said animal's arterial blood system. Circuit 10 comprises a deoxygenator 12 containing animal blood; a blood reservoir 15 for holding blood leaving the deoxygenator; a roller pump 18; an oxygenator 21; a gas pulse generator 35, and a cylinder 45 of oxygenating gas. These various elements are connected one to another by suitable tubing 26.

It will be understood that deoxygenator 12 may be a living animal, e.g., a young calf, in which case venous blood leaves the animal by way of a venous cannula and oxygenated blood is returned to the animal's arterial blood system by way of an arterial cannula. Alternatively, and quite conveniently for routine laboratory investigations, deoxygenator 12 may comprise an apparatus add carbon dioxide to, and reduce the concentration of oxygen in, the blood which enters it. Blood for laboratory investigations may be taken from a recently slaughtered animal. Blood to be oxygenated leaves deoxygenator 12 as indicated by arrow A and is returned to the deoxygenator is indicated by arrow B. Deoxygenator 12, when it is an apparatus as opposed to a living animal, may comprise any well-known oxygenator through the gas passageway of which is passed a mixture of deoxygenating gas usually comprising nitrogen, carbon dioxide, and oxygen, blood being simultaneously passed through the blood passageway thereof.

Blood from deoxygenator 12 flows under gravity into reservoir 15 which may be any convenient device having entry and exit ports. A flexible bag for such reservoir is useful inasmuch as the same can be easily squeezed and flattened in order to eliminate air therefrom prior to the introduction of blood into the circuit.

Blood is pumped from reservoir 15 to oxygenator 21 by any well-known pumping means 18. A roller pump, such as the one supplied by Sarns under Code Number 6002, is suitable for this purpose. The pumping means is preferably adjustable so that the rate of flow of blood may be adjusted as needed or desired.

Blood leaving pumping means 18 is pumped to oxygenator 21 which may be any membrane oxygenator comprising a microporous membrane, but is preferably of a form according to British Pat. No. 1,442,754 such as has been used in development of the present invention. Oxygenator 21 has a blood inlet 22, a blood outlet 23, a gas inlet 24, and a gas outlet 25. The oxygenator also includes a first conduit for flow therethrough of blood to be oxygenated, a second conduit for flow therethrough of an oxygenating gas, and a microporous membrane, each of the two conduits being defined at least in part by the microporous membrane. After leaving the oxygenator at blood outlet 23, oxygenated blood flows into deoxygenator 12.

An oxygenating gas of known composition, which may be either pure oxygen or a mixture of oxygen with another gas or gases, is supplied from gas containing cylinder 45. Associated with cylinder 45 is a combination pressure regulator and gauge 46 and a flow control valve 47. When, in accordance with the method of the present invention, it is desired to pulse oxygenating gas through the oxygenator, the oxygenating gas from supply cylinder 45 is fed through control valve 47 into means 35 for pulsing said oxygenating gas. Such means, hereinafter sometimes referred to as a gas pulse generator, comprise a solenoid valve 36 to which has been connected an electric timing device 40. The solenoid valve has a gas inlet 37 and a gas outlet 38. The electronic timing device sends electrical impulses, on a preselected timed basis, to the solenoid which responds to said electrical impulses to regularly open and close said valve. The opening and closing of the valve imparts the desired pulsatile flow to the oxygenating gas. The oxygenating gas enters oxygenator 21 through its gas inlet 24 and leaves the oxygenator at its gas outlet 25.

As will be seen in FIG. 1, the circuit has a venous blood sampling port 50 and an arterial blood sampling port 51. Gas leaving the oxygenator may be collected in a suitable collecting device at oxygenator gas outlet 25 or may be fed through tubing (not illustrated) into a gas chromatograph or like device for analysis. The apparatus also includes a two-way valve 42. Valve 42 is placed between oxygenating gas supply cylinder 45 and the gas pulse generator inlet 37, and preferably between flow control valve 47 and inlet 37. It will be understood that two-way valve 42 may be set so that oxygenating gas is directed through gas pulse generator 35 and prevented from flowing through portion 26a of tubing which bypasses the gas pulse generator. Alternatively, valve 42 may be set so that oxygenating gas is directed through portion 26a of the tubing and prevented from flowing through the gas pulse generator. Thus, the apparatus and circuit of FIG. 1 may be used to perform experiments in which the oxygenating gas is passed through the oxygenator under steady flow conditions or under pulsatile flow conditions.

The oxygenator circuit also includes a pair of two-way valves 27, 28. Two-way valve 27 is placed in the circuit just upstream of oxygenator blood inlet 22. Two-way valve 28 is placed in the circuit just downstream of oxygenator blood outlet 23. Valves 27, 28 can be set so that blood is either pumped through the oxygenator, in which case blood will not pass through section 26b of tubing between valves 27, 28, or pumped through the section 26b of tubing between valves 27, 28, in which case the blood by-passes the oxygenator.

Figure 2:
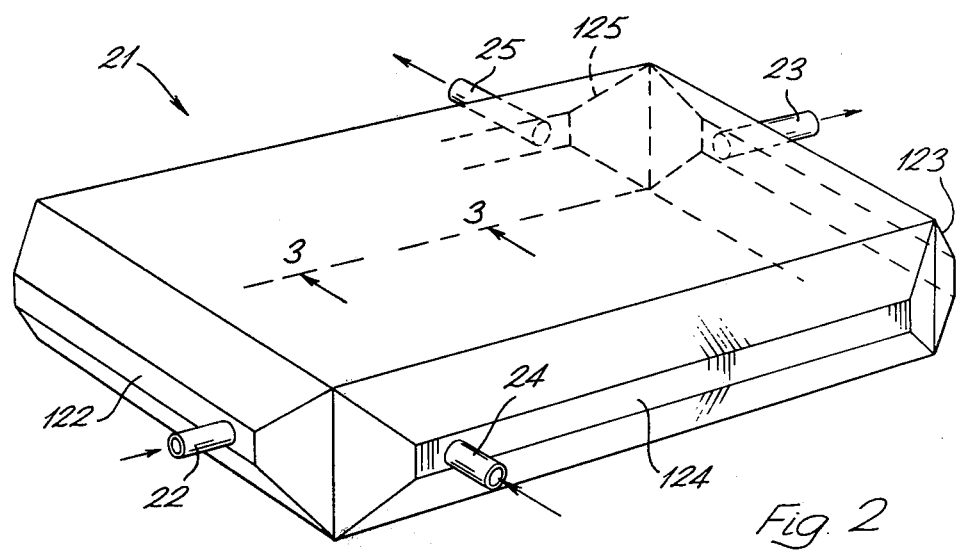
FIG. 2 is a perspective view of part of FIG. 1.
Figure 3:
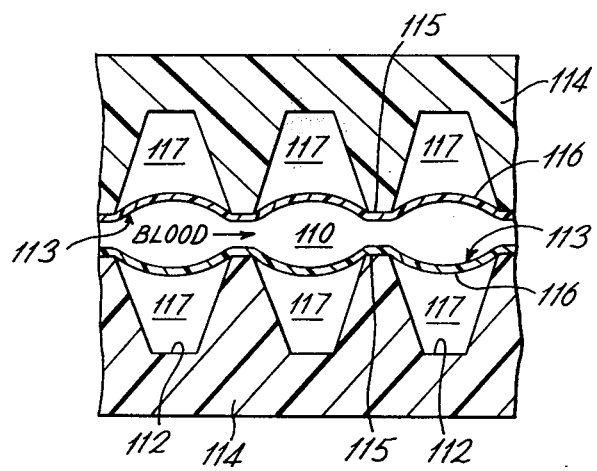
FIG. 3 is an enlarged cross-section taken along line 3—3 of FIG. 2.

Referring to FIGS. 2 and 3, there is illustrated further detail of the oxygenator of FIG. 1. Oxygenator 21 comprises a first conduit 110 for flow of blood therethrough and a second conduit for flow of oxygenating gas therethrough. First conduit 110 is defined by a pair of microporous membranes 113 which are spaced from each other and which each comprise a sheet of polytetrafluoroethylene having a thickness of 65±5 microns and a mean pore size of 0.3 microns. Each of membranes 113 is supported on a series of ridges 115 provided in rigid plastic support plates 114. Each membrane further comprises furrows 116 whose bottoms are spaced from the interior base 112 of support plates 114. The membranes are secured in known fashion, e.g., by use of an adhesive, to the ridges of their perspective support plates. The aforementioned second conduit for the flow therethrough of an oxygenating gas comprises a series of gas flow channels 117 which are defined by the spaces between furrows 116 and support plates 114. The vertical distance from base 112 to the top of ridges 115 is about 1.78 mm., while the vertical distance from the bottoms of furrows 116 to base 112 is about 1.14 mm. The ratio of pitch to depth of furrows 116 may vary; but is conveniently 4:1.

As seen in FIG. 3, support plates 114 are vertically spaced from each other and their alignment is such that ridges 115 of the plates are vertically aligned. Typically, the aligned ridges of the two plates are spaced about 0.4 mm. apart. The vertical spacing of the support plates is maintained by the use of suitable spacing strips (not shown) which are sealed to the membranes at their side edges to form a membrane envelope which is the blood conduit through which is passed blood to be oxygenated.

Oxygenator 21 further comprises a blood distribution chamber 112 communicating on the inlet side of the oxygenator with first conduit 10 and having a blood inlet 22. There is a corresponding blood distribution chamber 123 communicating on the outlet side of the oxygenator with first conduit 110 and having a blood outlet 23. There is a gas distribution chamber 124 communicating on the inlet side of the oxygenator with gas channels 117 and having a gas inlet 24. There is a gas distribution chamber 125 communicating on the outlet side of the oxygenator with gas channels 117 and having a gas outlet 25. Oxygenator 21 used in the experiments reported herein had one blood conduit 110 and may thus be described as a "single channel" oxygenator, and the conduit for flow of oxygenating gas comprised about two hundred gas channels 117. It will be appreciated that all materials which contact the blood should be blood compatible and non-toxic.

The data disclosed by the tables of FIGS. 4 and 5 was obtained from experiments run with the oxygenating circuit and apparatus illustrated in FIGS. 1-3. The following preliminary steps were carried out in preparation for all experiments, whether such experiments involved the passage of oxygenating gas under steady flow conditions or under pulsatile flow conditions.

Fresh whole mammalian blood, preferably not more than forty-eight hours old, was obtained and heparinized to a clotting time at least twice that of the unheparinized blood. The heparinized blood is put into deoxygenator 12. Two-way valves 27, 28 were set so that blood by-passed oxygenator 21. Pump 18 was then turned on and the blood passed, at a selected flow rate, from deoxygenator 12 into reservoir 15, then into pump 18, then through the tubing comprising the circuit and back into deoxygenator 12. The blood did not, at this time, flow through oxygenator 21. The blood passageway of the oxygenator was primed by filling it with 0.9% by weight aqueous saline. The gas passageway of oxygenator 21 was ventilated by passing the oxygenating gas therethrougn. A deoxygenating gas comprising a mixture of carbon dioxide, oxygen and nitrogen was passed through the gas passageway of deoxygenator 12. The composition and/or flow rate of deoxygenating gas was adjusted, in accordance with well known procedures, so that the partial pressure of $CO_2$ in the blood (p $CO_2$) leaving the deoxygenator was about 45 mm Hg. and the oxygen saturation of the exiting blood was about 65%. The haemoglobin level in the circulating blood was maintained at approximately 12 gm. %, the haemoglobin concentration being adjusted by the addition of isotonic solution or packed cells. When the above steps had been completed, two-way valves 27, 28 were set so that the blood circulated through oxygenator 21. A sample of blood is taken at venous sampling port 50 and checked for oxygen saturation. If necessary, the composition of the deoxygenating gas mixture was adjusted so that the following steady state (venous) conditions were obtained in the blood entering oxygenator inlet 22: % $O_2$ saturation=65%±5%, $pCO_2$=45 mm. Hg.±5 mm. Hg; pH=7.4±0.1. These checks and adjustments were repeated until the above mentioned conditions (i.e., conditions at the inlet into the oxygenator) were established in steady state operation.

After steady state oxygenator inlet conditions had been attained, samples were taken as follows. Samples of blood entering and leaving the oxygenator were taken simultaneously. Part of each of these blood samples were analyzed in a blood gas analyzer (available commercially from Corning as Model No. 165) to determine blood pH, blood partial pressure of oxygen ($pO_2$), and blood partial pressure of carbon dioxide ($pCO_2$). The remaining portion of each blood sample was analyzed for % oxygen saturation and total haemoglobin content in a CO-oximeter (such as the one commercially available from Instrumentation Laboratories, Inc. As Model No. IL 182).

After the above preliminary steps, the illustrated apparatus was operated with valves 27 and 28 set to pass blood through the oxygenator, but with valve 42 set so that the oxygenating gas by-passed the gas pulse generator. This operation confirmed that, in a blood oxygenator comprising a blood passageway and an oxygenating gas passgeway, each of which passageways is defined at least in part by a microporous membrane, the rate of transfer of carbon dioxide from the blood through the microporous membrane into the stream of oxygenating gas is not adequate to maintain the ratio $r_{CO_2}/r_{O_2}$ within the desired range.

The details and results of one such operation are shown by the table of FIG. 4. It will be seen that samples of venous blood, arterial blood, and effluent gas were taken simultaneously at periodic intervals. Venous blood, i.e. blood from deoxygenator 12 about to enter oxygenator 21 through blood inlet 22, was sampled at venous sampling port 50. Arterial blood, i.e., blood which had just left oxygenator 21 through blood outlet 23, was sampled at arterial sampling port 51. Effluent gas, i.e., the gas which had just left oxygenator 21 through gas outlet 25, was sampled at that outlet. The venous and arterial blood samples were analyzed for pH, $pCO_2$, $pO_2$, % $O_2$ saturation, and total haemoglobin content as described hereinabove. The effluent gas flow rate was determined by use of a spirometer (available from Benedict-Roth as Model No. 6449-M10) and was analyzed for volume percent (Vol. %) carbon dioxide concentration via gas chromatography. The composition of the oxygenating gas from supply tank 45 was already known, but a sample thereof could be taken at some convenient point prior to it entry into oxygenator 21 at gas inlet 24 and the sample analyzed, e.g., by gas chromatography, if required.

Sampling was effected on a periodic basis, generally at about fifteen minute intervals, and the operation lasted for about three hours. Elapsed time; blood pH, $pO_2$, $pCO_2$, total haemoglobin content, composition of effluent gas are shown in FIG. 4. The rate of transfer of carbon dioxide (in ml./min.) was calculated by multiplying the volume % $CO_2$ in the effluent gas by the rate of flow, in ml./min., of the effluent gas and the results are listed at the right-hand side of FIG. 4.

As can be seen from FIG. 4, the carbon dioxide transfers rates averaged 11.89 ml./min. and the oxygen transfer rates averaged 27.05 ml./min. Thus, when oxygen gas was passed through the oxygenator under steady flow conditions, the ratio of the average rate of transfer of carbon dioxide to the average rate of transfer of oxygen was 0.45 which is considerably and significantly below the average physiologic value of 0.8:1 characteristic of normally functioning lungs.

A further operation was carried out to confirm the advantages of pulsing the oxygenating gas as it flows through an oxygenator comprising a microporous membrane. This further operation was generally similar to that just described except that two-way valve 42 was set to pass the oxygenating gas through gas pulse generator 35 and thereby impart a pulsatile flow to the stream of oxygenating gas passing through oxygenator 21. The generator 35 was operated with the timing device 40 set to energise the solenoid of valve 36 at a frequency of 60 cycles/minute and at an off-on ratio of 0.25. It will be understood that when valve 36 is closed, the flow of oxygenating gas from gas pulse generator outlet 38 is stopped and the pressure of the oxygenating gas in the gas pulse generator and in that portion of the circuit upstream thereof is increased. When valve 36 opens in response to the signal from timing device 40, oxygenating gas flows from the gas pulse generator under the force of the pressure which was built up during the time interval when valve 36 was closed. The result of this is that the oxygenating gas is caused to flow through oxygenator 21 in pulsatile flow. In other words, at some point in time, i.e., when valve 36 is in the closed position, the pressure of the oxygenating gas in oxygenator 21 is relatively low or is in the process of declining from a relatively high value to a relatively low value; at another point in time, i.e., when valve 36 is in its open position, the pressure of the oxygenating gas is relatively high or is in the process of increasing from a relatively low pressure to a relatively high pressure. Thus, there is an interval when the pressure of the oxygenating gas in oxygenator 21 is lower than the average pressure and a subsequent interval when the pressure of the oxygenating gas in the oxygenator is higher than the average pressure.

The details and results of this further operation are tabulated in FIG. 5, from which it will be seen that the carbon dioxide transfer rates averaged 29.2 ml./min. and the oxygen transfer rates averaged 29.31 ml./min. (It is to be noted that the first sampled oxygen transfer rate in FIG. 5 is low because of the high % $O_2$ saturation in the venous blood flow at that time, and the former rate was accordingly omitted in calculating the average oxygen transfer rate.) Thus, when oxygen gas is passed through the oxygenator under pulsatile flow conditions, the ratio of the average rate of transfer of carbon dioxide to the average rate of transfer of oxygen is 0.99. This value is very much higher than the corresponding value obtained when oxygenating gas was passed through the oxygenator under steady flow conditions and is at the upper end of the range for the average physiologic value of 0.8:1 to 1:1 characteristic of normally functioning lungs.

Aside from the data and results discussed in connection with the above-described operations, further experiments have shown that, when oxygenating gas is pulsed through the oxygenator, the rate of transfer of carbon dioxide increases as the integrated flow rate of the oxygenating gas is increased.

Although, as demonstrated by FIG. 5, excellent rates of transfer of carbon dioxide were obtained when the oxygenating gas was pulsed at a frequency of 60 cycles/minute, it should be understood that the oxygenating gas pulse frequency may be varied without departing from the spirit and scope of the invention. Experiments have shown that beneficial results can be obtained with pulse frequencies in the range of 30–120 cycles/minute. At frequencies below about 30 cycles/minute, the rate of transfer of carbon dioxide may not be sufficient to achieve the desired ratio of the rate of carbon dioxide transfer to the rate of oxygen transfer. There appears to be little, if any, advantage to pulsing the gas at frequency in excess of 120 cycles/minute. Based on the work which has been done so far, it is preferred to employ a gas pulse rate of from about 50 cycles/minute to about 100 cycles/minute.

Also, the off-on ratio of the pulse gas generator can be varied.

It will be recognised that various other modifications may be made without departing from the spirit and scope of the present invention. For example, the oxygenating gas may be pulsed by use of a mechanically operated valve rather than by the electrically timed solenoid valve which was used in the initial development. As another alternative the oxygenating gas may be fed from the supply cylinder to the oxygenator through a piece of flexible tubing and the flow of the gas can be interrupted by a push cam which, at selected time intervals, stops the flow of the oxygenating gas through the flexible tubing.

Yet another alternative, mentioned earlier, is the use of a piston pump connected in parallel witnh a steady flow gas supply. This is illustrated schematically in FIG. 6 in which an oxygenator is denoted at 21 with inlets and outlets 22 to 25, as in FIG. 1, and with the piston pump denoted at 50.

I claim:

1. A method of oxygenating blood and removing carbon dioxide therefrom, such method comprising flowing blood through a first conduit at least partly defined by a microporous membrane, flowing oxygenating gas through a second conduit adjacent to said first conduit at least partly defined by said membrane, and pulsing said gas as it flows through said second conduit, so that oxygen is transferred from said second to said first conduit and carbon dioxide from said first to said second conduit, the rate of carbon dioxide transfer being maintained at a higher level than otherwise occurs without said pulsing.

2. A method according to claim 1 wherein said pulsing is effected by interrupting said gas flow.

3. A method according to claim 1 wherein said pulsing is effected by applying a primary flow of said gas to said second conduit and superimposing, in parallel manner relative to said second conduit, a secondary pulsatile flow on said primary flow.

4. A method according to claim 1 wherein said gas is pulsed at a frequency of at least 30 cycles/minute.

5. A method according to claim 1 wherein said gas is pulsed at a frequency in the range from about 30 to 120 cycles/minute.

6. A method according to claim 1 wherein said gas is pulsed at a frequency in the range from about 50 to 100 cycles/minute.

7. A method according to claim 1 wherein said gas is pulsed to provide successive periods of relatively increased and decreased levels of gas supply which periods are in a ratio of up to about 4.

8. A process according to claim 1 wherein said gas is pulsed to produce pressure changes of about 30 mm Hg in said flow.

9. A process according to claim 1 wherein said gas is pulsed to produce pressure changes in the range from 20 to 30 mm Hg in said flow.

* * * * *